(12) United States Patent
Chariff

(10) Patent No.: US 8,136,531 B2
(45) Date of Patent: Mar. 20, 2012

(54) DEVICE AND METHOD FOR TREATING MUSCULO-SKELETAL INJURY AND PAIN BY APPLICATION OF LASER LIGHT THERAPY

(76) Inventor: Mark D. Chariff, Miami Lakes, FL (US)

( * ) Notice: Subject to any disclaimer, the term of this patent is extended or adjusted under 35 U.S.C. 154(b) by 894 days.

(21) Appl. No.: 11/696,776

(22) Filed: Apr. 5, 2007

(65) Prior Publication Data

US 2007/0260297 A1 Nov. 8, 2007

Related U.S. Application Data

(60) Provisional application No. 60/746,668, filed on May 8, 2006.

(51) Int. Cl.
*A61B 19/00* (2006.01)
(52) U.S. Cl. .............................. 128/898; 607/88; 607/89
(58) Field of Classification Search .............. 607/88–92, 607/108, 109, 111; 606/2, 3, 9; 128/898
See application file for complete search history.

(56) References Cited

U.S. PATENT DOCUMENTS

| | | | | |
|---|---|---|---|---|
| 4,930,504 A | * | 6/1990 | Diamantopoulos et al. | 607/88 |
| 5,053,033 A | | 10/1991 | Clarke | |
| 5,161,526 A | * | 11/1992 | Hellwing et al. | 607/89 |
| 5,445,146 A | * | 8/1995 | Bellinger | 607/89 |
| 5,594,745 A | * | 1/1997 | Oka | 372/21 |
| 5,696,780 A | | 12/1997 | Pieterse | |
| 2002/0095142 A1 | | 7/2002 | Ming | |

FOREIGN PATENT DOCUMENTS

| | | |
|---|---|---|
| DE | 101 00 857 | 8/2002 |
| WO | WO2004/036705 | 4/2004 |

OTHER PUBLICATIONS

Lumenis Brochure, publication date unknown Lumenis Brochure, Re: Laser Absorption and Tissue Penetration, publication date unknown.
Esnouf A., et al., "Depth of Penetration of an 850nm Wavelenth Low Level Laser in Human Skin", *Acupunt. Electrother. Res.* 2007; 32(1-2): 81-6 (Abstract only).
Abdo A., et al., "NIR Light Penetration Depth in the Rat Peripheral Nerve and Brain Cortex" *Conf. Proc. IEEE Eng Med Biol Soc.* 2007; 1:1723-5 NIR (Abstract only).
Dai T., et al., "Comparison of Human Skin Opto-Thermal Response to Near-Infrared and Visible Laser Irradiations: A Theoretical Investigation" *Phys. Med. Biol.* Nov. 7, 2004; 49(21):4861-77, (Abstract only).
Ackermann G., et al., "Correlations Between Light Penetration into Skin and the Therapeutic Outcome Following Laser Therapy of Port-wine Stains" *Lasers Med. Sci.* 2002; 17(2):70-8, (Abstract only).
Topping A., et al., "Does Low Penetration of Human Skin by the Normal Mode Ruby Laser Account for Poor Permanent Depilatory Success Rates?" *Lasers Med. Sci.* 2001; 16(3):224-9, (Abstract only).

(Continued)

*Primary Examiner* — Ahmed Farah
(74) *Attorney, Agent, or Firm* — Feldman Gale, P.A.; Walter C. Frank

(57) ABSTRACT

A laser therapy device and method of treatment for treating musculo-skeletal pain. The device and treatment employ a composite laser beam comprised of multiple frequencies of laser energy.

13 Claims, 2 Drawing Sheets

OTHER PUBLICATIONS

Shackley DC., et al., "Light Penetration in Bladder Tissue: Implications for the Intravesical Photodynamic Therapy of Bladder Tumours", BJU Int. Oct. 2000; 86(6):638-43, (Abstract only).

Fraenkel M., et al., "Measurement of the Energy Penetration Depth into Solid Targets Irradiated by Ultrashort Laser Pulses", Phys. Rev. E. Stat. Phys. Plasmas Fluids Relat. Interdiscip. Topics Feb. 2000; 61(2):1899-903, (Abstract only).

Kolari PJ., et al., "Poor Penetration of Infra-red and Helium Neon Low Power Laser Light into the Dermal Tissue", Acupunct. Electrother. Res. Jan.-Mar. 1993; 18(1):17-21, (Abstract only).

* cited by examiner

DEVICE AND METHOD FOR TREATING MUSCULO-SKELETAL INJURY AND PAIN BY APPLICATION OF LASER LIGHT THERAPY

CROSS-REFERENCE TO RELATED APPLICATION

This application for utility patent claims priority from Provisional Patent Application 60/746,668, filed on May 8, 2006, entitled: Device and Method for Treating Musculo-Skeletal Injury and Pain by Application of Laser Light Therapy.

STATEMENT REGARDING FEDERALLY SPONSORED RESEARCH OR DEVELOPMENT n/a

FIELD OF INVENTION

The present invention lies in the field of medical devices. In particular, it relates to the treatment by means of laser light of musculo-skeletal pain and wounds.

BACKGROUND OF THE INVENTION

Laser Light Therapy is well known in the treatment of a wide variety of medical conditions whereby the laser emits light at certain specific bio-effective frequencies. In various applications, it is used to treat musculo-skeletal pain caused by injury or chronic and acute conditions. A non-exhaustive list of the conditions treated by Laser Light Therapy includes whiplash, arthritis, migraine, lower back pain, tendonitis, carpal tunnel syndrome, tennis elbow, golfer's elbow, strains, sprains, knee, neuropathy, ankle and foot pain, TMJ, and soft tissue injuries. The therapy is also useful in treating and promoting wound healing.

Depending on the nature and extent of the treated injury, the effects of Laser Light Therapy may be either curative or palliative. Where soft tissue injury is involved, such as in the case of sprains or strains, the device appears to promote direct healing of the injured tissue. If the injury is structural as in the case of a torn ligament or bone fracture, the device provides palliative relief and may be used in conjunction with other treatments.

Laser light consists of discrete coherent light of a wavelength from a narrow spectrum of electromagnetic radiation ("EMR"). In general it is amplified EMR that is monochromatic, collimated, polarized and concentrated in a relatively defined location or spot. Low Level Lasers are considered to be lasers varying in power intensity from 1 mW to 500 mW and are commonly used in therapy. The properties of laser light in general are such that it penetrates the surface of the skin without, or when desired with only limited, associated heating. Laser light is well known to possess and direct bio-stimulating energy to the cells of the body which, in turn, facilitates and enhances the body's own healing and pain regulating mechanisms.

Laser Light Therapy appears to be an effective treatment because of its ability to enhance the maintenance or restoration of biological systems to proper conditions of homeostasis and its ability to initiate or amplify the body's own regenerative systems. Injury or other chronic conditions may have a deleterious affect on cellular systems and thereby compromise the cell's ability to regulate its functioning or to effect repairs where tissue has been damaged. Where cell membranes have been damaged, laser light therapy enhances receptor-mediated movement across the cell membrane. Thus it has a positive effect on the cell's ability to maintain or restore proper function, repair of the cell's enzyme systems and re-establish the proper balance of proteins, ions or carbohydrates to allow the cell to function normally. Often, the addition of energy to the cell system can restore proper function and balance as the cell is re-stabilized and homeostasis is restored.

In laser therapy, photonic energy is emitted from a laser source. The energy, in the form of photons, is absorbed by photo acceptor sites on the cell membrane. This in turn triggers the cell's biochemical pathways which initiate the transmission of a variety of signals initiating, inhibiting or accelerating a variety of biological processes. These processes include inflammation reactions, cell growth or pain blocking. Furthermore, photonic energy is known to promote and optimize anti-inflammatory and immuno-stimulative effects.

In general, the significant biological effects of laser light are known to include cell growth stimulation and cell regeneration which, positively affect connective tissue, tendons, bone, muscles and nerves. Laser light therapy promotes revascularization of damages or injured tissue leading to positive therapeutic effect. Further, laser light therapy is known to improve microcirculation in injured or damages tissue thereby relieving, for example, edemas, and facilitating the healing in treating torn or damages muscle tissue. It further acts to inhibit inflammation of afflicted areas by inhibiting the ability of leukocytes to trigger increasing inflammation responses. It is also known to reduce fibrous tissue formed in response to injury.

At the cellular level, Laser Light Therapy is also well-known to increase the levels of adenosine tri-phosphate (ATP) produced by the mitochondria of the cell. One effect of laser light is to promote and stimulate cytochromes, including porphyrin, to produce singlet oxygen during the creation of ATP. ATP, in turn, plays a critical role in transporting energy within the body's cells and tissue and thus greater levels of ATP act to stimulate higher levels of cellular activity. Increased ATP production promotes increased levels of various growth factors and higher levels of protein synthesis, which are key for cellular repair and functioning.

Under the stimulation of laser light energy, greater degrees of cell proliferation have been observed. Other beneficial effects include increased levels of endorphin release leading to pain relief, both acute and chronic. Increased lymphocytic activity leading to a stronger immune response is also observed. Another well known beneficial effect of laser therapy is the promotion of revascularization of the blood and lymph vessels in response to therapy. This is particularly useful in treating edema and contusions related to injury or trauma.

Presently, lasers of particular wavelengths are known in the prior art. None, however, disclose the art of a composite beam comprised of laser energy emitted at wavelengths of 532 nm, 808 nm and 1064 nm which this device in its preferred embodiment does. An example of this is U.S. Pat. No. 5,464,436 which uses laser light within the range of 800-870 nm, more preferentially 830 nm, to treat a variety of musculo-skeletal injuries and conditions. Other therapeutic devices used for treating injuries and musculo-skeletal pain include laser emitting light at frequencies in the range of 635 nm at approximately 5 mW of power. While relatively powerful lasers emitting light at wavelengths of 532 nm are used by surgeons in the removal of tattoos and by dentists for bleaching or whitening teeth, the use of such frequencies is little known in the treatment of musculo-skeletal pain and injury. An example of one patent that does employ a similar frequency is U.S. Pat. No. 6,582,454 to Yayama. While Yayama does use a beam emitted at a frequency of 530 nm in connection with other beams, none of the other beams include frequencies of the infrared spectrum. Laser light at that frequency is known to be readily absorbed by hemoglobin. Therefore it is used in ablating blood vessels and treating other cosmetic skin conditions caused by blood vessels such as port wine stains. It is further known to readily penetrate the skin.

Furthermore, in lasers that are used to treat musculo-skeletal pain, the emitted therapeutic light is typically of one wavelength only, typically ranging from 635 nm to 980 nm. While multi-diode lasers may be used, the diodes usually emit identical frequencies of EMR and thus merely increase the energy deposited without varying the spectrum of the treating light source. Where multiple-diode lasers have been employed that emit different wavelengths, such as in U.S. Pat. No. 4,669,839, only one wavelength has been selected for its therapeutic quality and effect. A second wavelength is typically used as a guide beam to assist in directing the therapeutic beam. When multiple frequencies are used to treat musculo skeletal conditions as in the '454 patent, the frequencies have not included similar combinations of frequencies as disclosed herein and in fact differ in their characteristics. The instant device for example includes infrared wavelengths which allow greater penetration of the tissue than visible wavelengths as in the '454 patent. Furthermore, in the instant invention, the laser beams do not intersect and then diverge as in Yayama but rather are emitted as a composite beam and this too facilitates the deeper penetration of the target tissue than Yayama. Not only does the composite beam penetrate more deeply than Yayama without diverging, each component beam of the composite beam simultaneously strikes the same target tissue and from the same angle. Furthermore, in at least certain embodiments of this device, at least two (2) composite beams form an octave, here the 532 nm beam and the 1064 nm beam or at least approximate an octave.

SUMMARY OF THE INVENTION

The present invention uses multiple beams of different frequencies to provide improved beneficial therapeutic and palliative effects of laser therapy. Preferably, at least one of the multiple frequencies should fall within the 532 nm range. Heretofore the therapeutic effects on musculo-skeletal conditions of lower frequency lasers in the 532 nm range has gone unappreciated. Indeed there is currently no therapeutic device or treatment practiced employing the use of a laser beam emitting EMR at that frequency. Thus one aspect of the present invention is the use of EMR at the heretofore unused 532 nm frequency in the treatment of musculo-skeletal injury and pain.

Further, the treatment of such conditions by a laser beam composed not of a single therapeutic frequency but from energy of different, simultaneously emitted, therapeutic wavelengths is not known or practiced. The present invention thus provides a therapeutic method and device for treating pain and tissue damage employing both features. The present invention generates a multi-frequency beam reaching transcutaneously into afflicted tissue without causing significant heating and employing energy of a heretofore unused therapeutic, lower frequency in combination with energy of higher frequencies. Based upon observed treatments using the present invention, the use of a laser beam emitting a variety of frequencies as in the present invention appears to have a synergistic effects on the treatment of musculo-skeletal pain and injury.

It should be appreciated, furthermore, that use of this device is not limited to the treatment of humans. Indeed, the disclosed device should also prove useful in treating any mammals.

The present invention in one embodiment relies upon a lasing source that generates a laser beam having a frequency of 532 nm at a power of up to 65 mW. Additionally, the beam, according to one embodiment of the invention, transmits additional EMR at wavelengths of 808 nm and 1064 nm and at a combined power of no more than 435 mW but closer to 200 mW. Further the beam produced is relatively dispersed in order to minimize any associated thermal effects on the areas of the body treated. The device may be specially manufactured or adapted from preexisting commercially available devices.

It should be readily appreciated by those skilled in the art that a composite laser beam having the characteristics set forth herein may be generated by other means. For example, individual laser devices or diodes could be used to generate isolated beams which through the use of beam splitters could then be merged to form a composite laser beam. Additionally a variety of mirrors or other optics could be employed to merge multiple beams so that same could be emitted as a composite beam through a single aperture.

The specific frequencies are not considered limitations of the device and surrounding frequencies in combination may prove equally effective. Thus, a device according to the present invention may include EMR from higher or lower frequencies around the ranges disclosed herein. EMR from the yellow bandwidth, ranging up to 594 nm, which is also known to be readily absorbed by hemoglobin, may also be included. So, too, may intermediate frequencies in the range of 808 nm to 980 nm be encompassed in the device, whether emitted from a single diode or multiple diode laser. Further, frequencies in the range of 1064 nm to 1300 nm may similarly be encompassed in the device.

Additionally, the power output of the laser is not considered to be a limitation, and more powerful or less powerful lasers may also be employed according to the instant invention. For example, lasers incorporating 1-5 Watt pump diodes and generating energy beams of similar frequencies may also yield similar beneficial results.

The selection of a laser beam composed of energy of lower, heretofore unused wavelengths in combination with higher frequencies has been observed to yield highly positive results in the treatment of various musculo-skeletal conditions, including but not limited to those identified above, when therapeutically applied.

In the first aspect of the method for treatment according to the invention, the health care provider diagnoses the afflicted area of the patient to determine specific treatment points associated with the condition for which relief is sought. The treatment may be applied to a wide variety of musculo-skeletal conditions and structures of the body. The present invention may beneficially treat conditions including, but not limited to, inflammation, necrosis/gangrene, hematomas, edema, contusions, strains, sprains, avulsion, ruptures, arthritis and other chronic and acute pain. In addition the treatment may be used to promote wound healing. In the treatment, Laser Light Therapy targets a array of various tissue structures of the body that may be associated with the condition. These include skin, subcutaneous tissue, mucous membranes, muscle, tendon, the vascular system, the lymph system, joints of the skeletal system, the nervous system, as well as the periosteum.

Diagnosis may employ various examination techniques including: (1) palpation of the afflicted region to determine areas of sensitivity and tenderness; (2) visual observation including regions of swelling, redness or similar; (3) viewing of x-rays, MRIs or other imaging depictions; or (4) recourse to known or determined acupuncture points, and the tracing of the peripheral nerve supply of the affected tissue to its spinal source level. The second step involves treating the patient by applying the barrel of the laser device onto the afflicted area in an appropriate pattern and for an appropriate duration thereby applying a proper dosage of laser light. Many times, irradiating the damaged tissue will elicit a pain response from the patient, confirming the existence of pathology. Where wounds are treated, the therapy is somewhat modified in that the barrel of the laser is not directly applied to the afflicted area. The wound area is irradiated as well as the healthy tissue on the periphery. During this phase, the above outlined treatment may be repeated a number of times in response to the results observed by the health care provider and feedback from the patient. The treatment may further incorporate the application of light therapy along the peripheral nerves and concluding at the spinal segment supplying the afflicted areas. Depending on the severity of the condition and the results of initial treatment, follow up visits may be appropriate over a period of days and weeks. More specific treatment protocols that represent variations on this general treatment are described below.

DETAILED DESCRIPTION OF THE PREFERRED EMBODIMENTS

Figure 1:
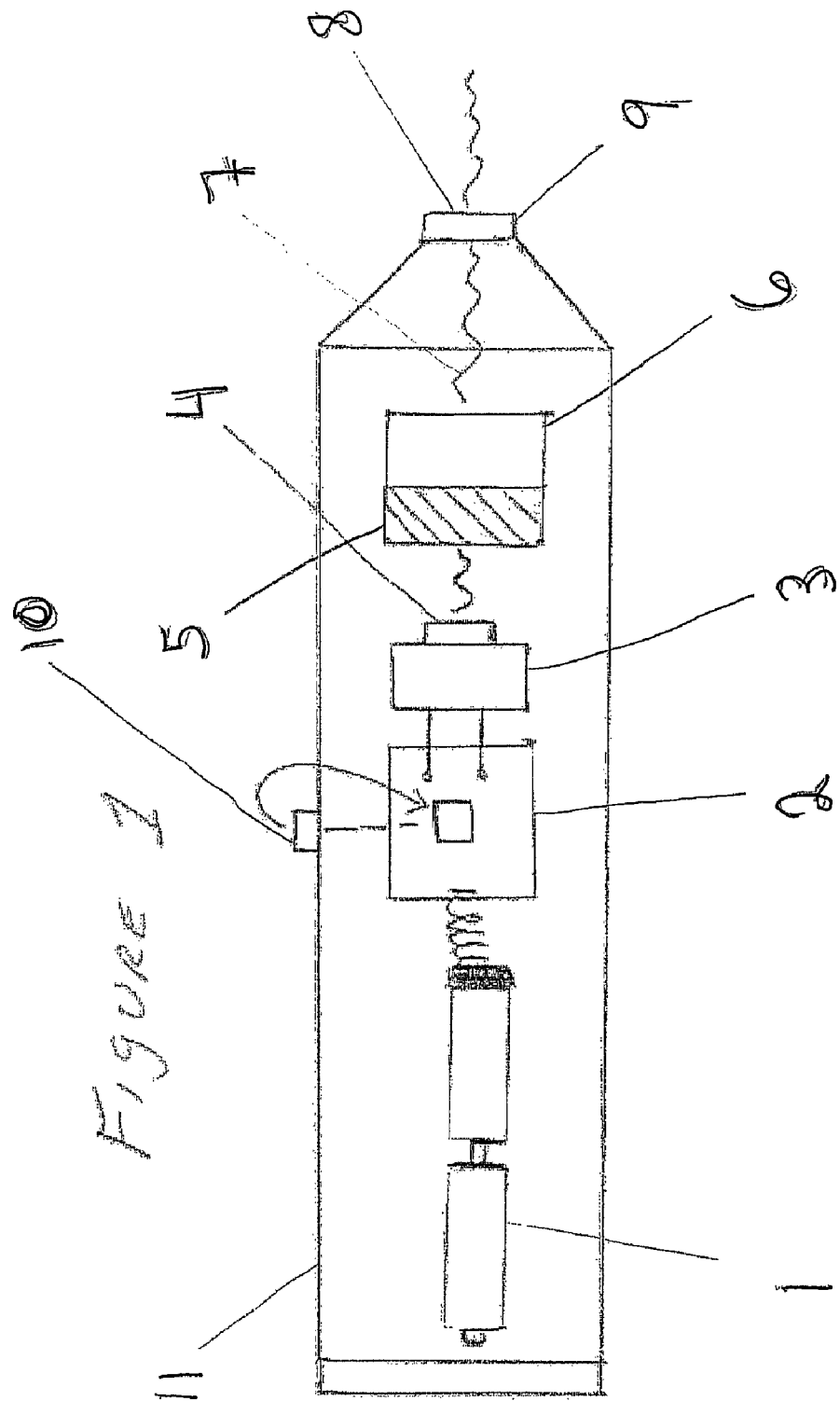
FIG. 1 shows a schematic of the device according to one aspect of the present invention

FIG. 1 shows the device according to one aspect of the present invention. In the device as shown, a power source, 1, is connected to a 500 mw driver board, 2. While standard AAA batteries are shown, it should be readily apparent to one skilled in the art that other power sources may be employed. A standard plug-in electrical connection, for example, could also be used. The power source is used to power the driver board, 2, here a 500 mW driver board. The driver board, 2, in turn powers an 808 nm pump laser diode, 3. The diode, 3, emits a beam through a microlens, 4. The resultant beam is then emitted through an NDYV04 crystal, 5, and thereafter through a KTP crystal, 6. The resultant composite laser beam is emitted through a collimating lens, 8, and then through a single aperture, 9. The resultant laser beam is comprised of laser energy emitted at approximately 532 nm, approximately 808 nm and approximately 1064 nm.

The device also incorporates a shut-off switch, 10, that allows the user to regulate the duration of the application of the composite beam and also to prevent the device from overheating and otherwise burning out the laser diode. The danger of overheating is controlled by the relatively short durations of the application. In other embodiments, the laser device may incorporate heat sinks, cooling fans or other mechanisms for regulating the thermal output of the device and controlling associated problems. The device as shown may be housed in a casing, 11, of suitable size and shape for being held in the hand of an operator.

In another embodiment of the invention the laser beam may be emitted as a pulse beam. Thus, the beam includes pulsed laser energy emitted at least at approximately 532 nm. Said composite beam may further included a beam emitted at approximately 808 nm and a beam emitted at approximately 1064 nm.

The device may also include associated meters or gauges showing information on the status of the device including its power level, the levels of its emitted light or similar information on the functioning of the specific device. The device may further be sold as part of a kit wherein the kit includes treatment protocols, maintenance protocols or other written materials that may focusing on the use of the device.

A composite beam of laser energy emitting energy at the frequencies claimed herein may also be prepared by modifying a commercially available laser such as a GaAlAs 808 nm Diode Pumped Solid State (DPSS) laser powered by a 500 mW driver. The device is fitted with suitable crystals to generate laser light of the appropriate, 532 nm, 808 nm and 1064 nm frequencies however commercially available laser devices do not emit such beams. The crystals may include a KTP (Potassium Titanium Oxide) crystal and an ND: YV04 (Yttrium Vanadate) crystals. DPSS lasers are equipped to filter energy from the 808 nm and 1064 nanometer frequencies and thus do not emit a composite beam. The device is modified by removing those filters and thereby emits electromagnetic radiation at those wavelengths in addition to the green laser light at 532 nm, something the device was incapable of doing as originally configured. The output of the laser shown in this embodiment consists of EMR as follows: up to 65 mW of 532 nm green laser light and as much as 435 mW of 808 nm and 1064 nm EMR. Further, the laser beam in this particular embodiment is emitted as a continuous wave rather than a pulsed beam. In other embodiments, however, pulsed beams may be generated and used.

Additionally, the focusing lens of the device is removed in order to generate a more diffuse beam which minimizes any thermal effect caused by the higher wavelength beams and the energy output of the device. The device shown is equipped with a shut-off switch which allows the health care provider to control the duration of the beam emission and ameliorate the risks of overheating the device. The device may be hand held when housed in a casing of suitable shape and size.

Figure 2:
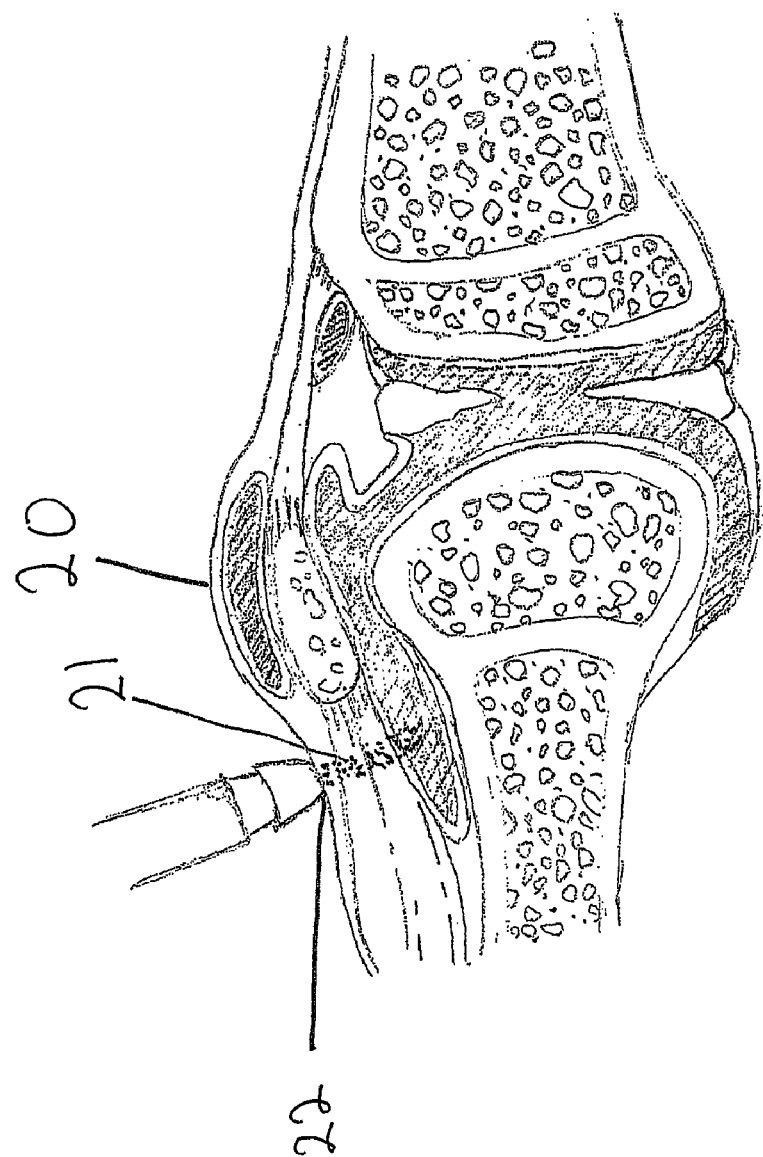
FIG. 2 shows the device in operation.

FIG. 2 shows a device according to the instant invention being applied to a condition under treatment, here a knee, 20. The beam, 21, which is comprised of energy at wavelengths of 532 nm, 808 nm and 1064 nm, is applied directly over the afflicted tissue at an angle of approximately 90°. Application at this angle will maximize penetration by the photonic energy of the dermal layers to varying depths according to the wavelength of the emitted energy. In treating musculo-skeletal pain, the tip of the laser device, 22, may be held directly against the treatment point for the afflicted area and applied in a linear, back and forth motion at a rate of approximately 1 inch every 3 seconds not to exceed a treatment duration of 30 seconds. The device is then turned off for at least approximately 5 seconds and the process is repeated for up to 10 times, depending on the extent and degree of injury and responsive feedback from the patient. Thus the dosage per treatment will usually range up to 150 Joules. Dosages vary per condition and severity, however, as prescribed by the health care provider. Further, actual dosage on the target tissue is variable with not all of the laser energy reaching the target tissue. Thus in many applications, the dosage at the surface of the skin significantly exceeds that on the target tissue.

As the therapy is administered, the laser deposits energy in the form of photons within the afflicted cells. While not wishing to attribute the beneficial results achieved by the invention to any specific theory or modality, it appears that the application of EMR in accordance with the invention stimulates the nerves and increases circulation to the area under treatment. In turn, this increases blood flow and oxygen to the area under treatment and thus additional endorphins are released and pain enzymes are blocked.

Depending on the condition being treated, various effects appear to contribute to the efficacy of the treatment. For treating musculo-skeletal conditions such as sprains or strains, and other inflammations, the therapy may be applied as described above. By compressing the tissue as pressure is applied to the epidermis of the patient, the underlying, afflicted tissue structures may be brought into a closer proximity to the energy beam. Thus the different frequencies may reach the target tissues and energize the associated cells.

In treating musculo-skeletal pain, the treatment protocol concludes with the application of therapeutic light along the peripheral nerves and into the spinal segment where those nerves terminate and connect to the Central Nervous System. Laser Light Therapy is believed to enhance receptor activity on cell membranes associated with the production of endorphins. Accordingly, bio-stimulation by laser light enhances the production of endorphins with a resulting decrease in pain associated with the underlying condition. In addition, laser light is known to decrease production of bradykinin, which is one of the main causes of pain. Further, laser light therapy suppresses the excitation of the unmyelinated C-fibers, thereby alleviating pain associated with musculo-skeletal injury.

In treating wounds, the above treatment may be somewhat modified since direct contact with the wound may cause pain or discomfort or otherwise negatively effect the healing of the wound. In treating wounds, the laser is held immediately above the afflicted region and healthy tissue around the periphery. Application of the Laser Light Therapy has a positive effect on the production of granulation tissue during the proliferative phase of repairs. It also stimulates increased collagen synthesis as well as the activation and migration of macrophages and fibroblasts to the area of injury. Further Laser Light Therapy encourages the proliferation of mast cells as well as increases in endothelial cells and keratinocytes. In addition, Laser Light Therapy may increase the transport of ions, including possibly calcium ions, across the cell membrane and increase the cell's ability to transmit signals bringing about cell repair. Furthermore, the above effects all enhance the body's regenerative system to bring about wound healing.

Several more specific treatment protocols are variations on the above generalized therapy regimen. For treatment of persistent headaches, for example, the health care provider treats peripheral triggerpoints, including mid trapezium and suboccipital muscles with the application of laser light therapy and then treats the area of perceived head pain both with the laser barrel head contacting the skin.

The device may also be used to treat traumatized gum tissue, e.g. from a tooth extraction. In those cases, the health care provider should splay the beam over the area of involvement for at least 90 seconds. There should be no skin contact with the end of the barrel. Skin contact can then be made to trace the branches of the trigeminal nerve.

For oral mucosal trauma, the same protocol is an effective treatment.

Where treating joint pain in a patient, the health care provider applies EMR through directly contacting the laser head to the surface of the area to be treated irradiating the joint space, tendon attachments and the attendant muscle belly(s) with EMR. There should be a further continuation of nerve tracing to the spinal segment supplying the joint structures.

In treating acute cervical spinal injury with spasm and stiffness, for example, caused by auto accident, lifting injuries, or similar, the specific protocol is as follows. With the patient in a sitting position and the health care provider standing behind patient, the laser head of the device is applied with pressure to the skin over the spinous processes, interspinous ligaments, posterior cervical muscles, sternocleidomastoid muscle and mid trapezium (bilaterally). The treatment commences with a slow sweeping motion over the above-described areas. During treatment, the patient may complain of stinging pain over area of greatest inflammation. This will occur even with no skin contact. The patient is instructed to turn head to tolerance in order to stretch the involved tissues as laser light treatment is applied.

For a lumbar injury, the patient stands while supporting weight with hands on a table or wall in front of the patient. The health care provider applies the laser head to the patient's skin and moves the beam over the lumbar muscles, and medially to the interspinous ligaments, and medially to the spinous processes, all performed in a caudal to cephalic and then reversed motion. The beam is also run along the posterior thighs and calves. During treatment, the patient is instructed to bend forward to tolerance in order to stretch involved tissues. If possible, in the treatment of all spinal conditions, treatment should be performed while the spine is loaded and not while the patient is recumbent.

In the case of patients suffering from radiculopathies caused by spinal nerve root dysfunction, precipitated by biomechanical pressure or altered local physiology, the treatment may consist of irradiating the entire neural pathway of the afflicted nerve, starting at the peripheral innervation and ending at the spinal segment that the nerve root exits from.

Furthermore, the treatment protocols may include variable dosages depending on the condition treated. Thus treatment dosages at the target tissue may include the following:

Treatment for Recent Injuries
Shoulder: 40-50 joules
Knee: 20 joules
Ankle: 40 joules
Conditions
Strains: 5-10 joules per point. 35-50 joules total treatment
Osteoarthritis
   Interarticular: 4-8 joules per joint
   Extra articular: 2-4 joules per point
Total Dosage
Ankle/Foot: 20-30 joules
Knee: 20-40 joules
Spine: 4-16 joules per vertebral motor unit, with additional treatment directed to the supporting musculature These ranges are rough guides for treating some target tissue in response to some conditions and injury, but they are not intended as limitations. Indeed, higher dosages have been observed to yield positive and, at times, improved results.

The embodiment of the device disclosed in FIG. 1 has been tested on various patients suffering from a variety of musculo-skeletal conditions. For example, a 45-year-old female with a severe sprain on the left lateral ankle was treated pursuant to the therapy protocol outlined above and with the device described in FIG. 1. Unable to walk due to pain and severe swelling, laser light therapy was applied to the afflicted ankle over a total treatment period of five minutes. The result was a 75% reduction in swelling and an immediate ability to walk on the affected ankle with minimal pain. The effects of the treatment were not diminished by time and the patient had a full recovery in less time than would be expected due to the nature of this injury.

A 30-year-old female suffering from a complete tear of the anterior cruciate ligament was also treated. The patient had difficulty walking due to the injury. After applying the treatment outlined above with the same device, the patient reported markedly less pain on ambulation, even though the device did not repair the severed ligament.

Further, a 60-year-old male with a severe intercostal muscle sprain was treated 2 weeks post injury duration. The patient, employed as an industrial air-conditioning mechanic was unable to perform job duties due to inability to fully extend left arm and twist trunk due to severe pain in the lateral rib cage. The patient was treated as set forth above with the same device over the affected area. Upon treatment, the patient was virtually asymptomatic and exhibited a full range of motion of the trunk and left arm. Follow-up research three days later revealed that the patient remained virtually asymptomatic.

Further, a nonagenarian patient who had suffered a fall injuring her lower back, left knee and left foot. In addition, she suffered in part from a persistent numbness on the sole and lateral aspect of her left foot. The neuropathy was treated by application of laser light from the device along the injured foot, knee, the sciatic nerve distribution network and at the lumbar spine. As a result of the therapy, the patient reported that normal sensation in the previously numb foot had been restored.

Another patient suffering a bilateral rotator cuff tear was also treated with the device as outlined above. Prior to treatment, the patient exhibited an extremely limited range of motion with the injured shoulder. Post treatment, the patient was able to fully extend the injured shoulder. Although the pain associated with the torn rotator cuff did return, the palliative effect was pronounced and treatment was considered successful.

What is claimed is:

1. A method of providing laser therapy to a patient comprising the steps of;
    diagnosing the patient's area of musculo-skeletal pain;
    providing a laser therapy device at or near the surface of the patient's skin proximate to said area of musculo-skeletal pain;
    causing said device to apply to said area of musculo-skeletal pain a composite laser beam comprised of beams emitted at a plurality of wavelengths including at least one beam emitted at a wavelength of approximately 532 nm, a second of said beams emitted at a wavelength of approximately 808 nm, and a third of said beams emitted at a wavelength of approximately 1064 nm; and
    manipulating said device in a pattern and for a duration over said area of musculo-skeletal pain;
    wherein the laser therapy device emitting the composite laser beam comprises a power source, a driver board, an 808 nm pump laser diode, a microlens, a NDYV04 lasing crystal, a KTP lasing crystal, a collimating lens, and a single aperture, said device when in operation emitting a composite laser beam through a single aperture.

2. A method of providing laser therapy to a patient according to claim 1, wherein the laser therapy device emits the composite laser beam as a pulse beam.

3. A method of providing laser therapy to a patient according to claim 1, wherein the laser therapy device is battery powered.

4. A method of providing laser therapy to a patient according to claim 1, wherein the laser therapy device has a total power output of no more than 2 W.

5. A method of providing laser therapy to a patient comprising the steps of;
    diagnosing the patient's area of musculo-skeletal pain;
    providing a laser therapy device at or near the surface of the patient's skin proximate to said area of musculo-skeletal pain;
    causing said device to apply to said area of musculo-skeletal pain a composite laser beam comprised of beams emitted at a plurality of wavelengths including at least one beam emitted at a wavelength of approximately 532 nm, a second of said beams emitted at a wavelength of approximately 808 nm, and a third of said beams emitted at a wavelength of approximately 1064 nm; and
    manipulating said device in a pattern and for a duration over said area of musculo-skeletal pain.

6. A method of providing laser therapy to a patient comprising the steps of;
    diagnosing the patient's area of musculo-skeletal pain;
    providing a laser therapy device at or near the surface of the patient's skin proximate to said area of musculo-skeletal pain;
    causing said device to apply to said area of musculo-skeletal pain a composite laser beam comprised of beams emitted at a plurality of wavelengths including at least one beam emitted at a wavelength of approximately 532 nm, a second of said beams emitted at a wavelength of approximately 808 nm, and a third of said beams emitted at a wavelength of approximately 1064 nm; and
    manipulating said device in a pattern and for a duration over said area of musculo-skeletal pain;
    wherein the laser therapy device has a total power output of no more than 2 W.

7. A method of providing laser therapy to a patient according to claim 6, wherein the laser therapy device has a total power output of no more than 500 mW.

8. A method of providing laser therapy to a patient according to claim 6, wherein the laser therapy device emits the composite laser beam as a pulse beam.

9. A method of providing laser therapy to a patient according to claim 6, wherein the laser therapy device is battery powered.

10. A method of providing laser therapy to a patient comprising the steps of;
    diagnosing the patient's area of musculo-skeletal pain;
    providing a laser therapy device at or near the surface of the patient's skin proximate to said area of musculo-skeletal pain;
    causing said device to apply to said area of musculo-skeletal pain a composite laser beam comprised of beams emitted at a plurality of wavelengths including at least one beam emitted at a wavelength of approximately 532 nm, a second of said beams emitted at a wavelength of approximately 808 nm, and a third of said beams emitted at a wavelength of approximately 1064 nm; and
    manipulating said device in a pattern and for a duration over said area of musculo-skeletal pain;
    wherein the laser therapy device administering laser light therapy comprises a 500 mW GaAlAs laser fitted with an ND:YV04 crystal and a KTP crystal wherein an infrared filter and focusing lens have been removed to provide the composite laser beam, said beam emitted over a relatively broad area.

11. A method of providing laser therapy to a patient according to claim 10, wherein the laser therapy device emits the composite laser beam as a pulse beam.

12. A method of providing laser therapy to a patient according to claim 10, wherein the laser therapy device is battery powered.

13. A method of providing laser therapy to a patient according to claim 10, wherein the laser therapy device has a total power output of no more than 2 W.

* * * * *